United States Patent [19]

Mikhail

[11] Patent Number: 5,766,262
[45] Date of Patent: *Jun. 16, 1998

[54] FEMORAL PROSTHESIS WITH SPACER

[76] Inventor: W. E. Michael Mikhail, 4203 Shamley Green, Toledo, Ohio 43623

[*] Notice: The term of this patent shall not extend beyond the expiration date of Pat. No. 5,683,395.

[21] Appl. No.: 647,805

[22] Filed: May 15, 1996

Related U.S. Application Data

[60] Provisional application No. 60/014,598 Mar. 29, 1996.

[51] Int. Cl.$^6$ .................................................. A61F 2/36
[52] U.S. Cl. .................................................. 623/23; 623/18
[58] Field of Search .............................. 623/18, 19, 22, 623/23

[56] References Cited

U.S. PATENT DOCUMENTS

| | | | |
|---|---|---|---|
| 4,341,206 | 7/1982 | Perrett et al. | 128/92 |
| 4,399,814 | 8/1983 | Pratt, Jr. et al. | 128/92 |
| 4,623,353 | 11/1986 | Buechel et al. | 623/23 |
| 4,642,124 | 2/1987 | Cooke | 623/23 |
| 4,678,471 | 7/1987 | Noble et al. | 623/16 |
| 4,686,972 | 8/1987 | Kurland | 128/92 |
| 4,706,659 | 11/1987 | Matthews et al. | 128/92 |
| 4,751,922 | 6/1988 | DiPietropolo | 128/92 |
| 4,770,660 | 9/1988 | Averill | 623/23 |
| 4,815,454 | 3/1989 | Dozier, Jr. | 128/92 |
| 4,827,919 | 5/1989 | Barbarito et al. | 623/22 |
| 4,846,161 | 7/1989 | Roger | 128/92 |
| 4,860,735 | 8/1989 | Davey et al. | 128/92 |
| 4,865,608 | 9/1989 | Brooker, Jr. | 623/23 |
| 4,873,969 | 10/1989 | Huebsch | 128/92 |
| 4,881,536 | 11/1989 | Noble et al. | 606/94 |
| 4,919,153 | 4/1990 | Chin | 606/93 |
| 4,919,673 | 4/1990 | Willert et al. | 623/23 |
| 4,919,679 | 4/1990 | Averill et al. | 623/23 |
| 4,963,155 | 10/1990 | Lazzeri et al. | 623/23 |
| 4,986,826 | 1/1991 | Roger | 606/82 |
| 4,994,085 | 2/1991 | Sawai et al. | 623/23 |
| 5,018,285 | 5/1991 | Zolman et al. | 29/465 |
| 5,021,063 | 6/1991 | Tager | 623/23 |
| 5,047,035 | 9/1991 | Mikhail et al. | 606/93 |
| 5,061,287 | 10/1991 | Feiler | 623/16 |
| 5,078,746 | 1/1992 | Garner | 623/16 |
| 5,108,405 | 4/1992 | Mikhail et al. | 606/96 |
| 5,192,283 | 3/1993 | Ling et al. | 606/93 |
| 5,211,666 | 5/1993 | Fetto | 623/23 |
| 5,258,033 | 11/1993 | Lawes et al. | 623/23 |
| 5,314,493 | 5/1994 | Mikhail | 623/23 |
| 5,376,124 | 12/1994 | Gustke et al. | 623/23 |
| 5,470,336 | 11/1995 | Ling et al. | 606/105 |
| 5,507,830 | 4/1996 | De Mane et al. | 623/23 |
| 5,507,832 | 4/1996 | Michielli et al. | 623/23 |

FOREIGN PATENT DOCUMENTS

| | | | |
|---|---|---|---|
| 2615097 | 5/1987 | France. | |
| 31 08 491 A1 | 3/1981 | Germany. | |
| 1653763 | 6/1991 | U.S.S.R. | 623/22 |
| 0 315 283 | 11/1988 | United Kingdom. | |

*Primary Examiner*—Michael J. Milano
*Assistant Examiner*—Tram Anh T. Nguyen
*Attorney, Agent, or Firm*—Emch, Schaffer, Schaub & Porcello, Co., L.P.A.

[57] ABSTRACT

The femoral prosthesis designed for use with a proximal spacer ensures that the prosthesis, when implanted in bone cement in a prepared femoral cavity, will have sufficient space between the prosthesis and the bone to receive an adequate thickness of bone cement.

34 Claims, 7 Drawing Sheets

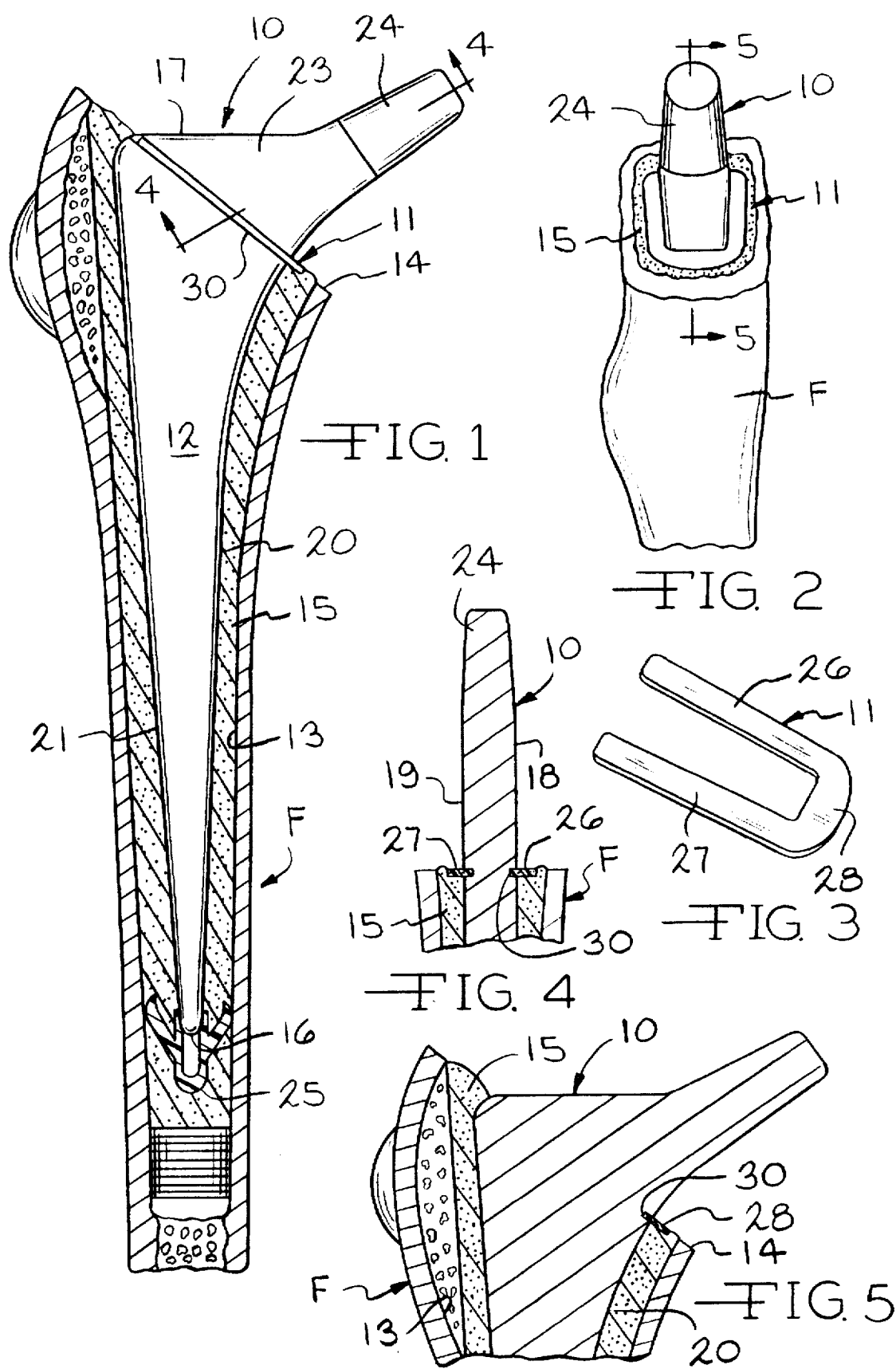

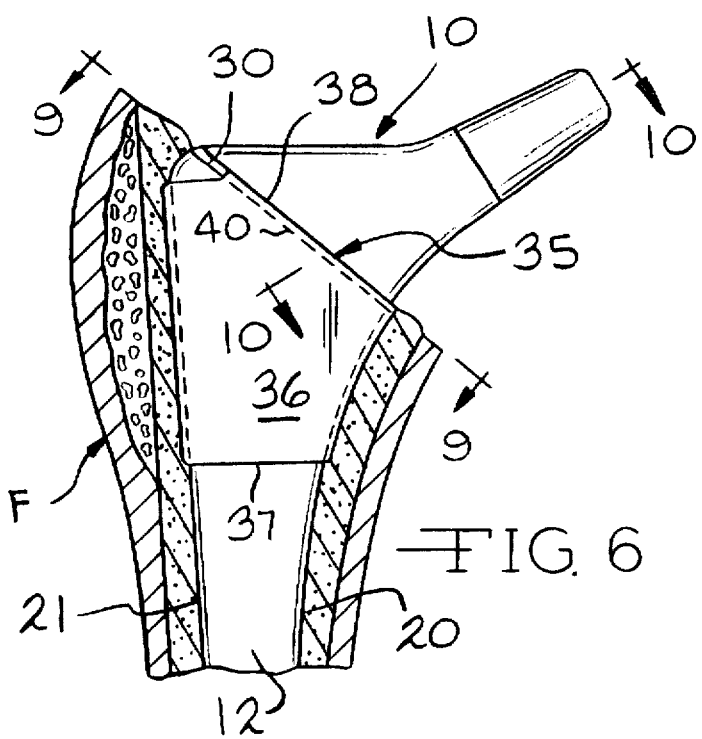
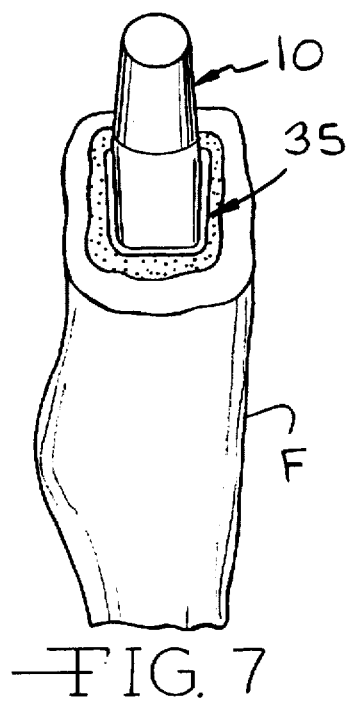
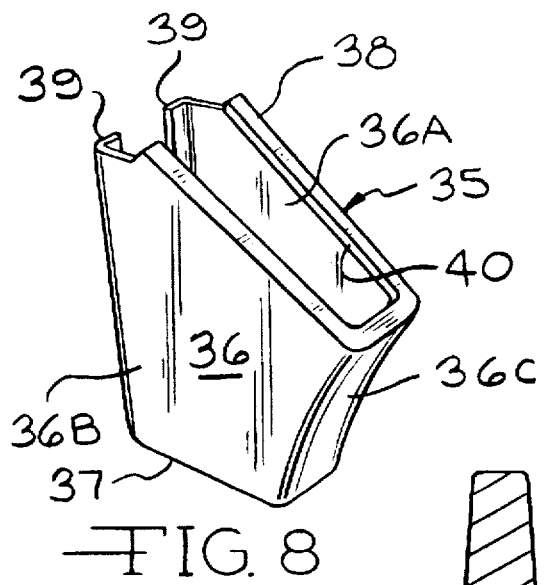
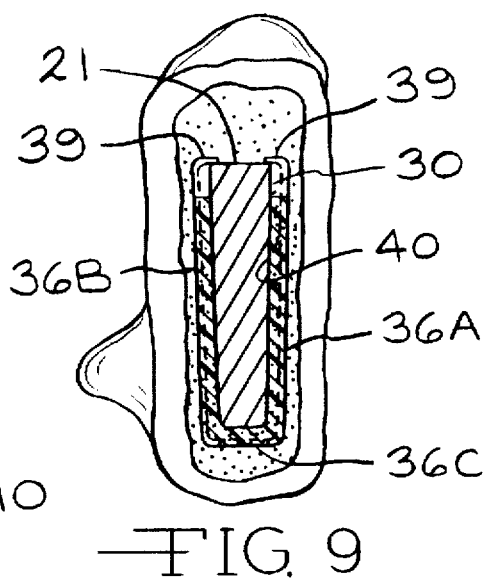
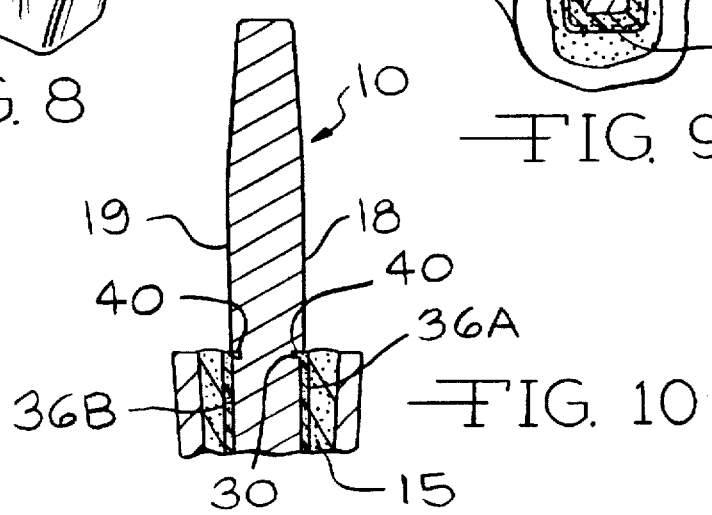

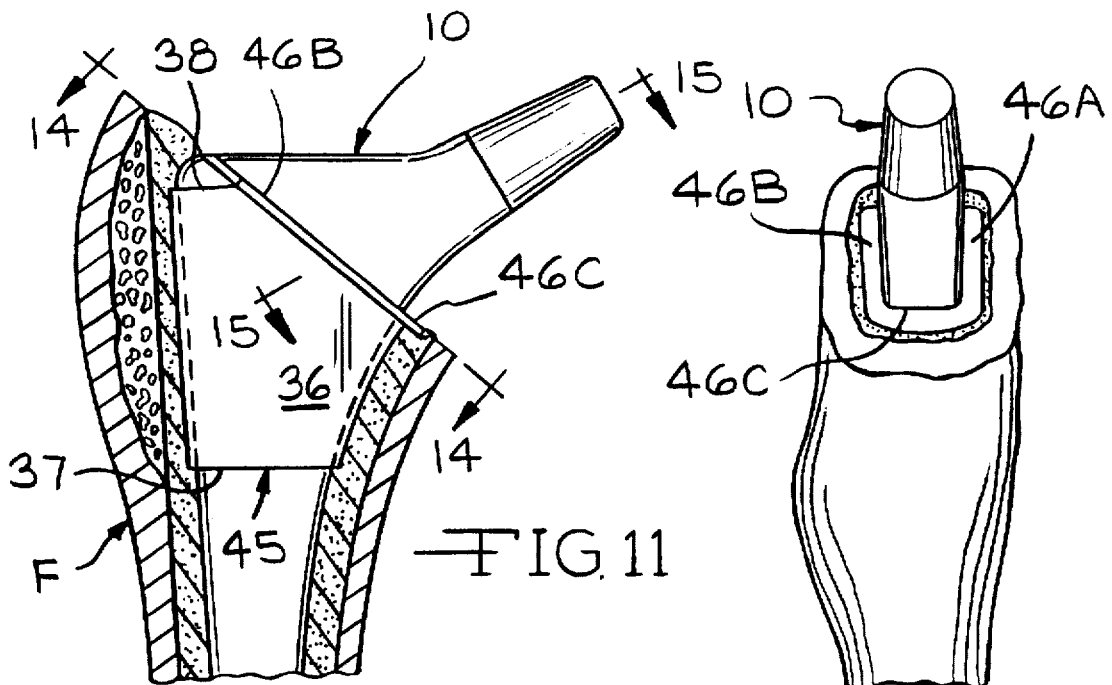
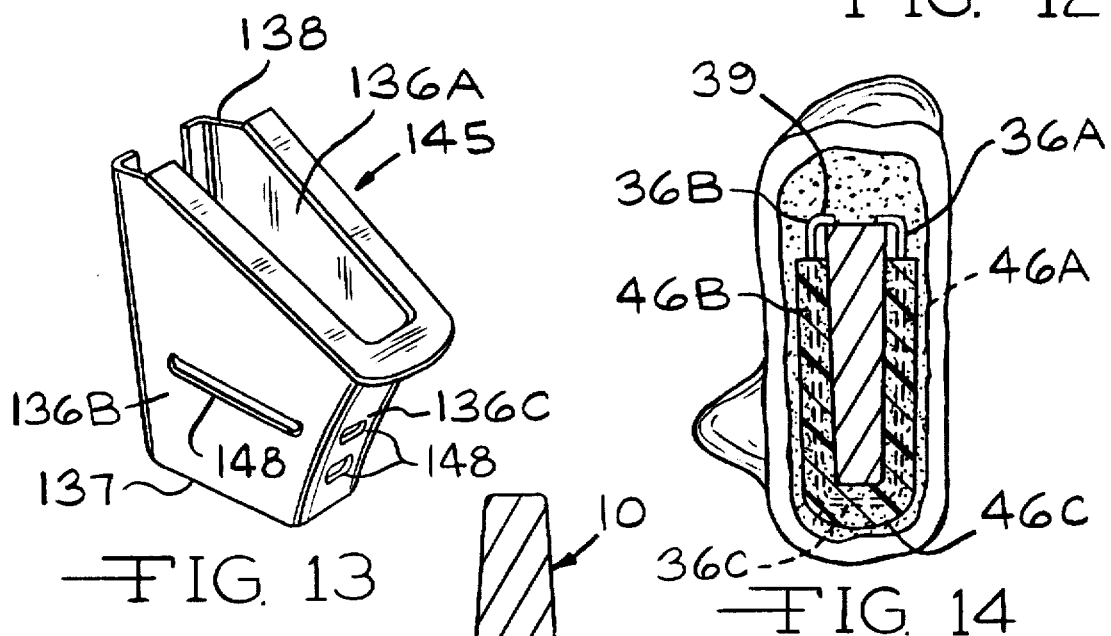
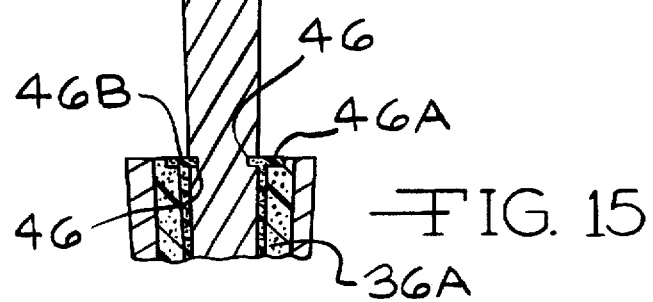

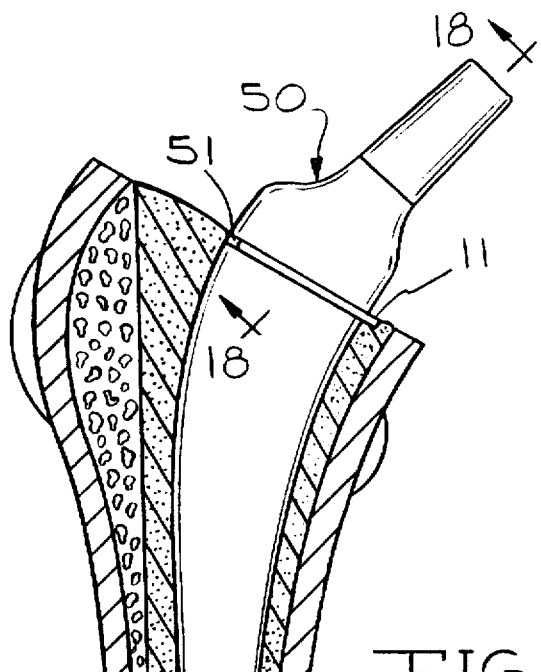
FIG. 16
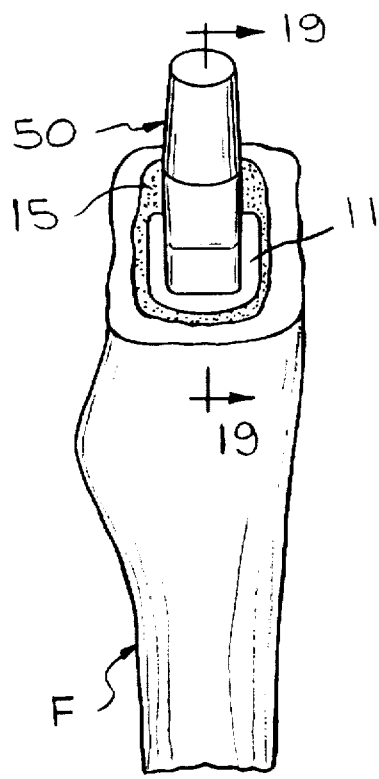
FIG. 17
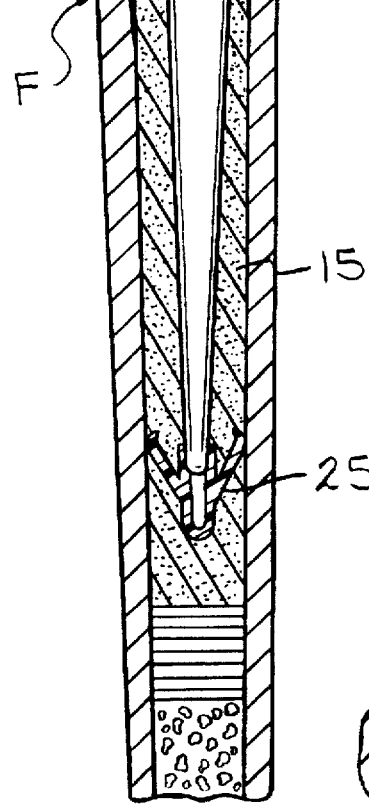
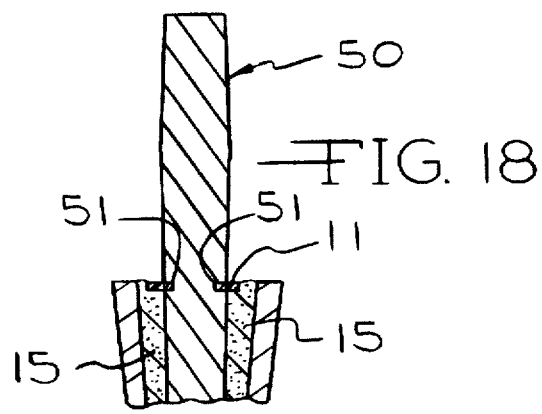
FIG. 18
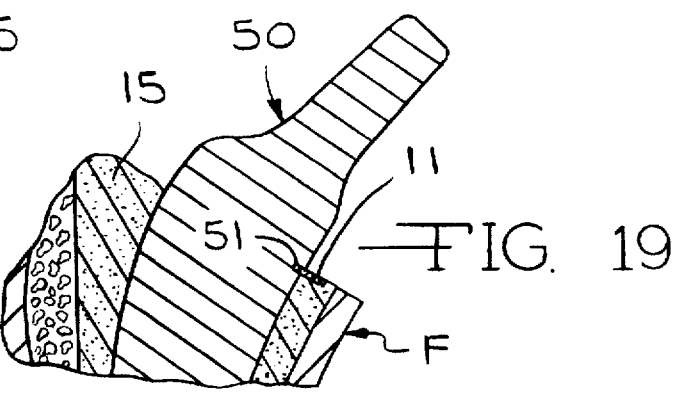
FIG. 19

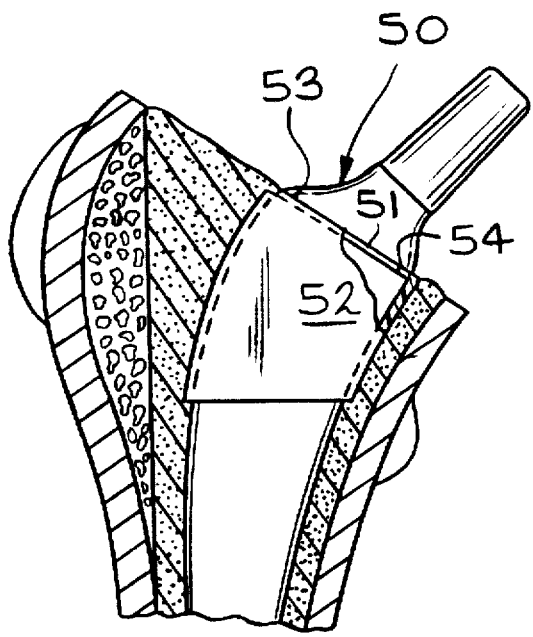
FIG. 20
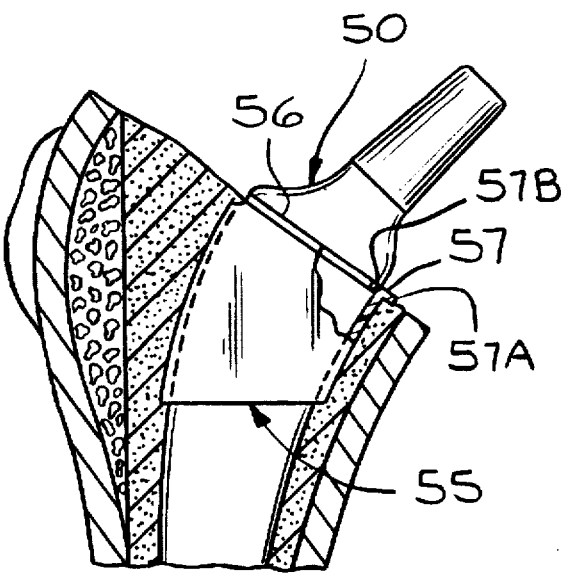
FIG. 21
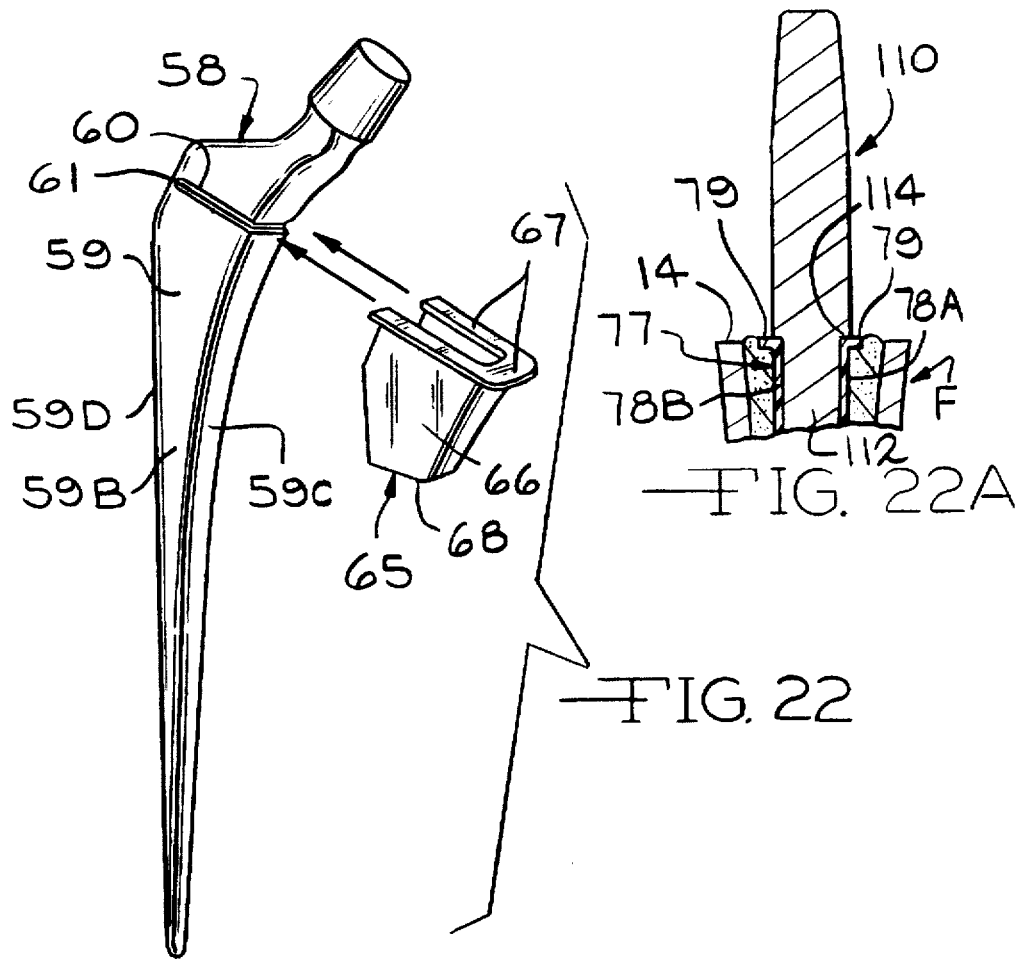
FIG. 22
FIG. 22A

2

FEMORAL PROSTHESIS WITH SPACER

CROSS REFERENCE TO RELATED APPLICATION

This application is related to Provisional patent application Ser. No. 60/014,598 filed Mar. 29, 1996.

DISCLOSURE OF THE INVENTION

The present invention is directed to a femoral prosthesis adapted for use with a spacer, to a universal spacer for use with a femoral prosthesis and to a combination of a femoral prosthesis and an attached spacer which, upon implantation in bone cement of a prepared femur, provides adequate space between the bone and the stem of the prothesis to allow an adequate thickness of bone cement throughout the circumference and length of the prothesis. The prosthesis preferably has a double tapered polished stem which is collarless. However, it can be also used with a prosthesis having a collar or a miniature collar.

According to one embodiment, the prosthesis is provided with a groove for retaining the spacer on the prosthesis in a proximal area of the stem near the shoulder. A distally facing surface of the spacer also compacts the cement as the prosthesis is inserted distally into the prepared cavity of the femur. The outer periphery of the spacer may contact the bone in one or more peripheral areas of the prepared cavity thereby providing space between the prosthesis and the wall of the prepared cavity to insure that the implanted prosthesis has adequate thickness of bone cement throughout.

The spacer of the present invention is universal in the sense that it can be utilized with femoral prostheses having a wide variety of designs and shapes for their stems, including a variety of cross-sectional configurations. Additionally, under one embodiment, the spacer can be trimmed to readily modify it to be used with a number of different shapes of femoral prosthesis stems.

Under a further embodiment, a spacer is provided for the distal end of a femoral prosthesis. Under other embodiments, the proximal spacer may be provided with a series of slots at its distal end permitting circumferential expansion in that area of the spacer to accommodate varying sizes and shapes of femoral prosthesis stems in that area and the distal spacer may be provided with a series of slots at its proximal end to permit circumferential expansion to accommodate varying sizes of stems in that area. The proximal spacer may be provided with gripping means for engagement with a femoral prosthesis.

BRIEF DESCRIPTION OF THE DRAWINGS

FIG. 1 is an elevational view, partly in section, showing the femoral stem prothesis and spacer combination of the present invention implanted in a prepared cavity of a femur.

FIG. 2 is a fragmentary view of the femoral stem prosthesis and spacer implanted as in FIG. 1 but rotated 90°.

FIG. 3 is a perspective view of the spacer.

FIG. 4 is a sectional view taken through line 4—4 of FIG. 1.

FIG. 5 is a sectional view taken through line 5—5 of FIG. 2.

FIG. 6 is a fragmentary view, partly in section, showing a modified embodiment implanted in a femur.

FIG. 7 is a view of the implanted embodiment of FIG. 6 rotated 90° from FIG. 6.

FIG. 8 is a perspective view of the spacer of FIG. 6.

FIG. 9 is a sectional view taken through line 9—9 of FIG. 6.

FIG. 10 is a sectional view taken through line 10—10 of FIG. 6.

FIG. 11 is a fragmentary view, partially in section, of yet another embodiment implanted in a femur.

FIG. 12 is a view of the implanted embodiment of FIG. 11 rotated 90° from FIG. 11.

FIG. 13 is a perspective view of a spacer similar to the spacer of FIG. 11 but with an additional modification.

FIG. 14 is a sectional view taken through line 14—14 of FIG. 11.

FIG. 15 is a sectional view taken through line 15—15 of FIG. 11.

FIG. 16 is an elevational view, partly in section, showing the spacer of FIG. 1 on a femoral prosthesis having a shape different from the prosthesis of FIG. 1 implanted in a femur.

FIG. 17 is a view of the implanted embodiment of FIG. 16 rotated 90° from FIG. 16.

FIG. 18 is a sectional view taken through line 18—18 of FIG. 16.

FIG. 19 is a sectional view taken through line 19—19 of FIG. 17.

FIG. 20 is a fragmentary sectional view showing a spacer similar to the spacer of FIGS. 6–10 on a prosthesis similar to the prosthesis of FIGS. 16–19.

FIG. 21 is a fragmentary sectional view showing a spacer similar to the spacer of FIGS. 11–15 on the prosthesis of FIGS. 16–19.

FIG. 22 is a perspective view showing the motion of attaching the spacer of FIGS. 11–15 to a femoral prosthesis.

FIG. 22A is a fragmentary sectional view showing a modified spacer in combination with a modified femoral prosthesis.

BRIEF DESCRIPTION OF THE INVENTION

Figure 23:
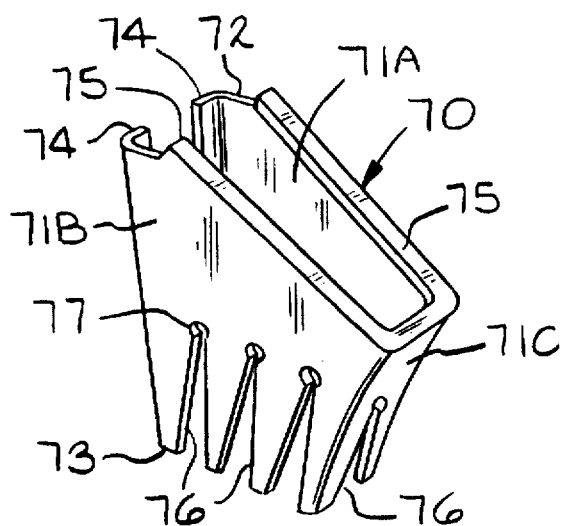
FIGS. 23–26 are perspective views of further embodiments of spacers.

Referring now to FIGS. 1 through 5, there is shown one embodiment of the femoral prosthesis 10 in combination with a spacer 11. The prosthesis 10 and spacer 11 are shown implanted in a prepared cavity 13 of a femur F. The femur F is shown with a cavity 13 extending to a proximal end 14, which cavity has been prepared to receive bone cement 15 and the prosthesis. The femoral prosthesis 10 and spacer 11 may be used with either primary or revision surgery and is shown implanted in bone cement 15 such as polymethyl methacrylate (PMMA) or other suitable cement.

The femoral prosthesis 10 has a stem 12 which extends from a distal end 16 to a proximal end 17. The stem 12 is double tapered and has a series of surfaces extending distally from the proximal end 17 including an anterior surface 18, a posterior surface 19, a medial surface 20 and a lateral surface 21. By double tapered it is meant that the anterior surface 18 tapers toward the posterior surface 19 and that the medial surface 20 tapers toward the lateral surface 21 as they approach the distal end 16.

The femoral prosthesis 10 is made of stainless steel, a cobalt chrome molybdenum alloy or other well known metals customarily used in hip joint replacement surgery. Preferably, the stem 12 is polished to a smooth finish.

The stem 12 is provided with a groove 30 having a breadth of 0.5 to 3 millimeters and a depth inwardly from the surface of approximately 0.5 to 3 millimeters, which groove 30 is positioned to be aligned with the proximal end 14 of the prepared femur when the prosthesis is properly implanted. The groove 30 extends inwardly from the anterior surface 18, the posterior surface 19 and the medial surface 20. The femoral prosthesis on the lateral surface 21 side is not provided with a groove.

The prosthesis 10 further includes a neck 23 which extends from the stem 12 at an angle in the range of 125° to 150°. Extending from the neck 23 is a Morse taper frustoconical portion 24. In FIG. 1, the distal end 16 of the femoral prosthesis 10 is shown received in a centralizer 25.

The spacer 11 is sized to be snugly received in the groove 30 and may be retained therein by frictional engagement. The spacer 11 includes an anterior leg 26 to be received in the groove 30 of the anterior surface 18, a posterior leg 27 to be received in the groove 30 of the posterior surface 19 and a medial leg 28 extending between the anterior leg 26 and the posterior leg 27 for engagement in the groove 30 of the medial surface 20. The breadth of the anterior leg 26, the posterior leg 27 and the medial leg 28 are such that the spacer 11 will extend outwardly from the anterior surface 18, posterior surface 19 and medial surface 20 a distance of 0.5 to 3 millimeters.

As can be readily seen from the drawings, the spacer 11 ensures that there will also be sufficient space between the femoral prosthesis 10 and the bone defined by the interior surface of the cavity 13 to ensure that the implanted prosthesis has an adequate thickness of bone cement throughout. The centralizer 25 at the distal end accomplishes this function at the distal end 16 of the prosthesis 10.

An additional advantage of the spacer 11 resides in the fact that that portion of the anterior leg 26, posterior leg 27, and medial leg 28 which face distally will engage the bone cement 15 upon implantation of the femoral prosthesis 10 therein and will serve to provide compaction to such bone cement 15 as the prosthesis is moved distally in the cavity 13 to the position shown in FIG. 1.

Preferably the spacer 11 is formed of PMMA which has the rigidity to be snugly received in the groove 30 and frictionally engaged therein and which mixes well with fresh PMMA used for the bone cement 15.

It will be noted particularly from FIG. 3 that the anterior leg 26 is disposed at a slight angle relative to the posterior leg 27 due to the tapering of the anterior surface 18 toward the posterior surface 19 as they approach the medial surface 20.

As will be readily appreciated, the spacer 11 is what may be termed to be a universal spacer in that it may be used with prostheses having a wide variety of shapes and configurations for the stem portions between their distal ends and the area of the groove.

The femoral prosthesis 10 of the present invention with its groove 30 and spacer 11 ensures that there will be an adequate thickness of bone cement throughout and encircling the stem 12 and insuring separation of the stem from the inner wall of the cavity 13 of the femur F. It is important that there be no voids in the bone cement 15 retaining the prosthesis 10 in the cavity 13. The pressurization achieved as a result of the distal surface of the spacer 11 engaging the bone cement 15 as the prosthesis 10 with the attached spacer 11 is moved distally into the cavity 13 further assists the bone cement in fully encapsulating the stem 12 and completely filling the cavity 13 with no voids in the bone cement 15. The femoral prosthesis and spacer of the present invention therefore minimize the chances of osteolysis and eventual mechanical failure of the implanted prothesis.

Referring now to the embodiment of FIGS. 6 through 10, there is shown a modified spacer 35 having a skirt 36 extending from a distal end 37 to a proximal end 38. The skirt 36 is configurated to follow the contour of the stem 12 in those areas of its anterior surface 18, posterior surface 19, and medial surface 20 which extend distally from the groove 30. Thus, the skirt 36 has an anterior wall 36A in surface-to-surface contact with the anterior surface 18 of the stem, a posterior wall 36B in surface-to-surface contact with the posterior surface 19 of the stem 12 and a medial wall 36C in surface-to-surface with the medial surface 20 of the stem 12. The skirt 36 is also provided with a pair of flanges 39 extending toward each other, one flange 39 extending from the anterior wall 36A and the other extending from the posterior wall 36B. The flanges 39 remain in spaced apart condition and, as may be seen in FIG. 9 follow the contour of the lateral surface 21 of the stem 12.

Extending inwardly from each of the anterior wall 36A, posterior wall 36B and medial wall 36C is a proximal flange 40 sized to be snugly received in the groove 30 of the stem. The spacer 35 may be readily positioned on the stem 12 by virtue of the resilience of the polymerized PMMA material by simply spreading apart the lateral end of the anterior wall 36A from the lateral end of the posterior wall 36B thereby moving the flanges 39 away from one another a sufficiently great distance to permit them to slide over the stem 12. Upon the flanges 39 reaching the lateral wall 21, the spacer 35 will spring back to its original shape with the opposing flanges 39 engaged to the lateral wall and with the inwardly directed proximal flange 40 engaging the groove 30 along the anterior surface 18, posterior surface 19 and medial surface 20.

The modified spacer 35 is preferably formed of PMMA in a thickness of 0.5 to 3 millimeters. Such thickness gives it (1) the flexibility to permit the lateral ends of the anterior wall 36A and the posterior wall 36B to be spread apart sufficiently to permit the flanges 39 to be positioned around the stem 12 and (2) the resiliency to snap back to engage the anterior wall 18 and posterior wall 19. Additionally, such thickness permits the spacer 35 to be trimmed with scissors or other cutting device if that is required to achieve a suitable fit with a particular style of femoral stem prosthesis. The feature of the spacer 35 being of a thickness and a material which permits the spacer to be readily trimmed, if necessary even by the surgeon during the operation, contributes significantly to the universality of the spacer.

Referring now to FIGS. 11, 12, 14 and 15, there is shown another embodiment of spacer 45. This embodiment of spacer 45 has a skirt 36 which is identical to the skirt of the embodiment of FIGS. 6–10. The spacer 45 of this embodiment is provided with a ledge 46 at the proximal end of the anterior wall 36A, posterior wall 36B and medial wall 36C. The ledge 46 extends both inwardly from such wall portions for engagement of the groove 30 and outwardly from such wall portions, with such outward extension being in the range of 0.5 to 3 millimeters.

As can be readily seen, ledge portion 46A extends inwardly and outwardly of anterior wall 36A, ledge portion 46B extends inwardly and outwardly of posterior wall 36B and ledge portion 46C extends inwardly and outwardly of medial wall 36C. Thus, while the embodiment of spacer 35 of FIGS. 6–10 provides a gap distally of the spacer distal end for new bone cement 15 at least as thick as the wall portions 36A, 36B or 36C, in the embodiment of FIGS. 11–15, the presence of the outer ledge portions 46A, 46B and 46C from the respective wall portions 36A, 36B and 36C will ensure that the thickness of the bone cement at the proximal end of the spacer will be at least as great as the distance from the stem to the outer edge of the ledge portions 46A, 46B and 46C.

FIG. 13 is a perspective view of a spacer 145 which is identical to the spacer 45 with he exception that some or all of the sidewall portions 136A, 136B and 136C are provided with one or more lateral slots 148. The slots 148 are particularly useful in those situations in which any of the sidewall portions 136A, 136B or 136C fail to have surface to surface contact completely through from the proximal end 138 to the distal end 137 as the slots 148 will permit the entry of bone cement into any gaps between the spacer 145 and the prosthesis thus filling any voids.

FIGS. 16–19 show the spacer 11 of FIG. 1 in use on a femoral prosthesis 50 having a different configuration and illustrates the universality of the spacer 11 which may be used with a wide variety of shapes of femoral prostheses. The prosthesis 50 has a groove 51 throughout major portions of each of its anterior, posterior and medial areas and the spacer 11 is snugly received in such groove 51. The prosthesis 50, contrary to the prosthesis 10 shown in the embodiment of FIGS. 1–15 does not necessarily having substantially flat anterior, posterior and medial surfaces in the area of the groove 51. Thus, the spacer 11 as well as the other embodiments of spacers can also be used with prostheses in which the anterior, posterior and medial surfaces in the area of the proximal end of the prosthesis are curved such that the cross sectional configuration of the prosthesis in that area is oval or oblong defined by a series of curves.

FIG. 20 illustrates a spacer 52 having a flange 54 at its proximal end 53 which extends only inwardly to engage the groove of a prosthesis 50 having a shape and groove 51 as shown in FIGS. 16–19.

FIG. 21 illustrates a spacer 55 having a proximal end 56 in which there is provided a flange 57 having an outwardly extending portion 57A as well as an inwardly extending portion 57B for engagement with the groove 51 of the prosthesis 50.

Referring now to FIG. 22, there is shown a femoral prosthesis 58 having a stem 59 with an anterior surface (not shown), a posterior surface 59B, a medial surface 59C and a lateral surface 59D. The prosthesis 58 has a groove 60 extending inwardly from the medial surface 59C and inwardly throughout major portions of the anterior wall and posterior wall 59B. The groove does not extend inwardly from the lateral surface and, as may be seen in FIG. 22, extends along the posterior surface 59B to an abutment 61 which is spaced a short distance from the lateral surface 59D.

A spacer 65 has a skirt 66 which extends from a proximal end to a distal end 68. The skirt 66 has posterior, anterior and medial portions with a flange 67 at the proximal end of the skirt 66 extending both inwardly and outwardly from each of such posterior, anterior and medial portions, with the inwardly extending portion engaged in the groove 60 and the outwardly extending portion assuring space between the prosthesis proximal end and the bone.

FIG. 22A shows a spacer 77 used in combination with a femoral prosthesis 110 having a stem 112. The prosthesis 110 is not provided with a groove but rather is provided with an enlargement defining distally facing shoulders 114 extending outwardly from each of the anterior and posterior surfaces. If desired, the shoulders 114 could extend completely around the circumference of the stem. The shoulders 114 follow a path such that upon implantation, they will be generally aligned with proximal end 14 of the femur F. The spacer 77 includes a skirt having an anterior wall 78A, a posterior wall 78B and a medial wall (not shown) extending between such anterior wall 78A and posterior wall 78B. The proximal end of each of said anterior wall 78A, posterior wall 78B and medial wall is provided with an outwardly extending flange 79 which is in abutting relationship with the shoulders 114 and which extends outwardly beyond the outer limit of such shoulders 114.

Referring now to FIG. 23, there is shown a further modified spacer 70 having a skirt with an anterior side wall 71A, a posterior side wall 71B, a medial side wall 71C each extending from a proximal end 72 to a distal end 73. Flanges 74 extend toward one another from each of the anterior side wall portion 71A and posterior side wall portion 71B.

A proximal flange 75 sized to be received in a groove of a femoral prosthesis extends inwardly from the proximal end of the medial side wall portion 71C and from a major portion of each of the anterior side wall portion 71A and posterior side wall portion 71B.

Each of the anterior side wall portion 71A, posterior side wall portion 71B and medial side wall portion 71C is provided with one or more slots 76 extending from the distal end 73 toward the proximal end 72. The presence of the slots 76 permits the distal portion of the spacer to spread out and become circumferentially enlarged if the size of the prosthesis in the area contacted by those portions of the spacer 70 is such as to cause such distal portion to spread out. The proximal end of each of the slots is provided with an arcuate portion 77 to minimize the effect of any stress concentration in the proximal end area of the slots 76 resulting from spreading or circumferentially enlarging the distal end of the spacer 70. The slots 76 are wider at the distal end 73 than at their proximal ends defined by the arcuate portions 77.

Figure 24:
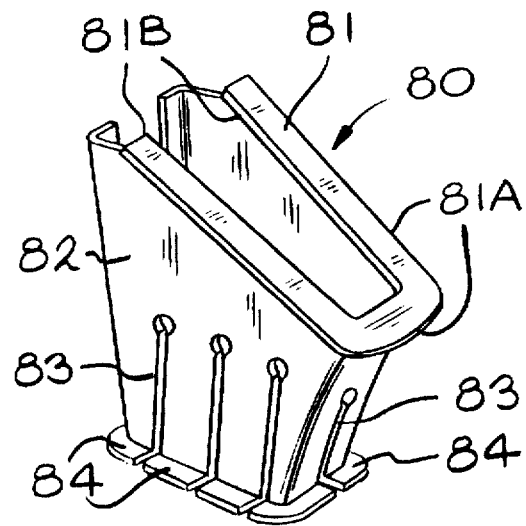

Referring to FIG. 24, there is provided a further embodiment of spacer 80 which is similar to the spacer 70 of the embodiment of FIG. 23 with the exception that the spacer 80 is provided with a flange 81 which has an outwardly extending portion 81A extending outwardly from each of the anterior, posterior and medial side walls as well as a portion 81B which extends inwardly from each of such side wall portions. Additionally, the skirt 82 is provided with slots 83 of generally uniform width and a plurality of outwardly extending flanges 84 at its distal end. The flanges 84 assist in maintaining that portion of the prosthesis spaced from the bone.

Figure 25:
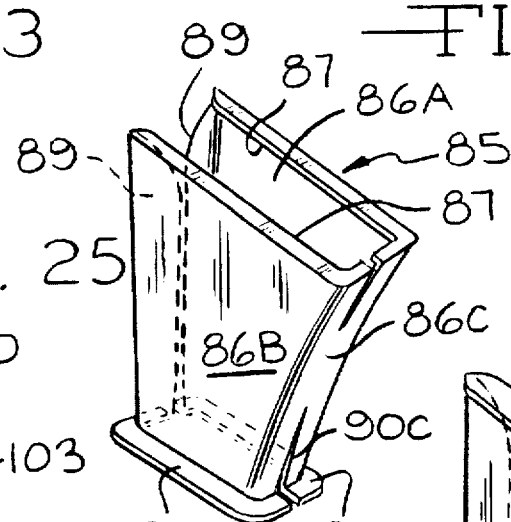

Referring now to FIG. 25, there is shown yet another embodiment of spacer 85 having a skirt with an anterior side wall portion 86A, a posterior side wall portion 86B and a medial side wall portion 86C, each of which has an inwardly extending flange 87 at the proximal end and an outwardly extending flange 91 at the distal end. Flanges 89 extend toward one another from each of the anterior wall portion 86A and posterior wall portion 86B. The distal end and the proximal end of the medial wall 86C may be provided with a triangular cut-outs 90C. If desired, similar triangular cut-outs could be formed in each of the anterior wall 86A and posterior wall 86B. Alternatively, the surgeon could, where desired, trim the spacer 85 to provide such cut-outs in the wall portions 86A and 86B.

Figure 26:
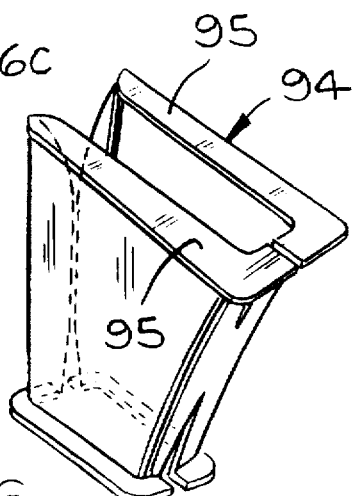

Referring now to FIG. 26, there is provided a spacer 94 which is identical to the spacer 85 of FIG. 25 except that the spacer 94 is provided with a proximal flange 95 which extends both inwardly and outwardly from the anterior, posterior and medial walls.

Figure 27:
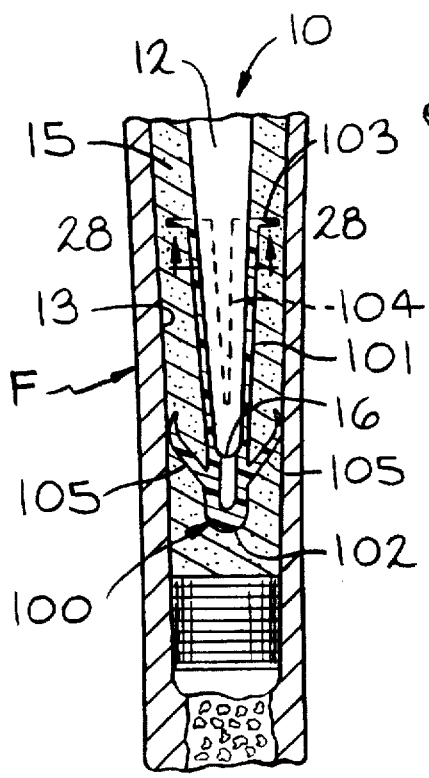
FIG. 27 is a sectional view of a further embodiment of spacer for the distal end of a femoral prosthesis.
Figure 28:
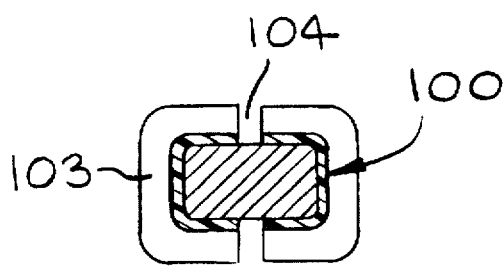
FIG. 28 is a sectional view taken through line 28—28 of FIG. 27.
Figure 29:
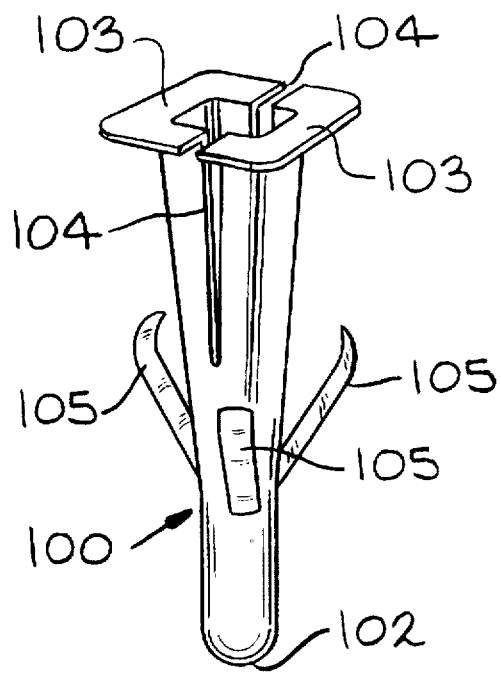
FIGS. 29–32 are perspective views of further embodiments of distal end spacers.

Referring now to FIGS. 27-29, there is provided a spacer 100 which has a side wall 101 which extends from a distal end 102 to a proximal end having an outwardly extending flange 103. The side wall 101 is provided with a pair of triangular slots 104 or cut-out portions which extend from the proximal flange 103 approximately one-half the distance to the distal end 102. As can be seen in FIG. 27, the slot 104 is wider at the proximal end and tapered. Additionally, the spacer 100 may be provided with a plurality of three or four wings 105 near the distal end.

The presence of the slots 104 permits those portions of the side wall 101 on each side of the respectively slots to be expanded outwardly as the distal end 16 of the stem is positioned therein and moved toward the distal end 102 of the spacer 100.

Figure 30:
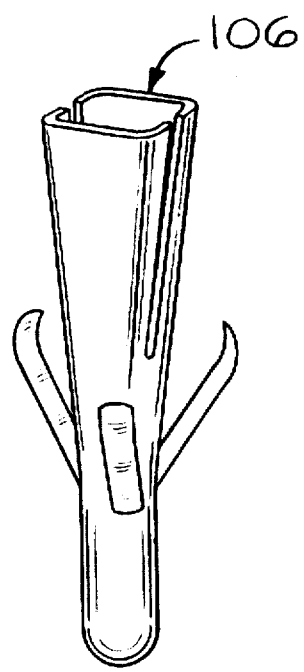

FIG. 30 is a perspective view of a modified distal spacer 106 which is identical to the spacer 100 except that there is no outwardly extending flange at its proximal end and the slots are in different circumferential area.

Figure 31:
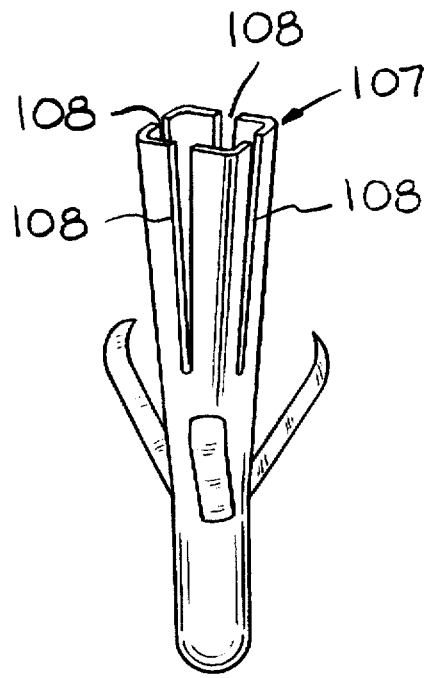

FIG. 31 is a view of another distal spacer 107 which is identical to the spacer 106 of FIG. 30 except that it is provided with four slots 108 extending distally from the proximal end.

Figure 32:
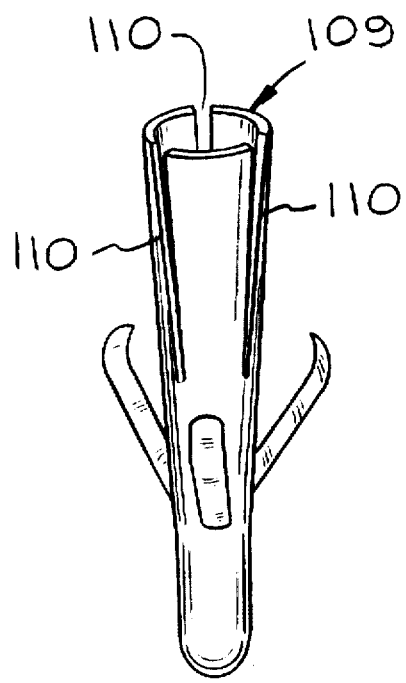

FIG. 32 is a perspective view of yet another embodiment of distal spacer 109 having a generally circular cross-sectional configuration at both its proximal end and its distal end and having three slots 110 extending distally from its proximal end.

Many modifications will become readily apparent to those skilled in the art.

I claim:

1. A femoral hip joint prosthesis for use in combination with bone cement comprising an elongated stem extending from a proximal end to a distal end and defining a first axis, said proximal end having a neck region which joins the stem at a juncture, said stem having anterior, posterior, medial and lateral surfaces and said surfaces tapering from said proximal end toward said distal end, a groove in the vicinity of said proximal end in each of said anterior, medial and posterior surfaces, each said groove in said anterior surface and said posterior surface extending substantially throughout the entire distance from said lateral surface to said medial surface and a spacer positioned in and substantially filling said groove and extending outwardly from each of said anterior, medial and posterior surfaces a distance at least equal to the intended thickness of said bone cement but no greater than the maximum thickness of bone cement in any area, said spacer including a skirt extending from a proximal end in the vicinity of said groove to a distal end, said skirt having (a) an anterior wall portion, a medial wall portion and a posterior wall portion in contact, respectively, with each of said stem anterior, medial and posterior surfaces and (b) a flange extending inwardly into said groove from each of said anterior wall portion, medial wall portion and posterior wall portion.

2. A femoral hip joint prosthesis according to claim 1 wherein said skirt includes portions engaged to said lateral surface.

3. A femoral hip joint prosthesis for use in combination with bone cement comprising:

(a) an elongated stem extending from a proximal end to a distal end and defining a first axis, said proximal end having a neck region which joins the stem at a juncture, said stem having anterior, posterior, medial and lateral surfaces and said surfaces tapering from said proximal end toward said distal end, a groove in the vicinity of said proximal end in each of said anterior, medial and posterior surfaces; and (b) a spacer positioned in said groove and extending outwardly from each of said anterior, medial and posterior surfaces, said spacer including a skirt extending from a proximal end in the vicinity of said groove to a distal end, said skirt having an anterior wall portion, a medial wall portion and a posterior wall portion in contact, respectively, with each of said stem anterior, medial and posterior surfaces and a flange at said skirt proximal end extending outwardly from each of said anterior wall portion, medial wall portion and posterior wall portion.

4. A femoral hip joint prosthesis according to claim 3 wherein said skirt is provided with apertures.

5. A femoral hip joint prosthesis according to claim 4 wherein said apertures comprise slots extending from said skirt distal end toward said skirt proximal end.

6. A femoral hip joint prosthesis according to claim 4 wherein said apertures comprise elongated slots spaced from said skirt distal end.

7. A femoral hip joint prosthesis according to claim 3 wherein said skirt is provided with an outwardly extending flange at said distal end.

8. A femoral hip joint prosthesis according to claim 7 wherein said skirt is provided with at least one slot extending from said distal end toward said proximal end.

9. A femoral hip joint prosthesis for use in combination with bone cement comprising (a) an elongated stem extending from a proximal end to a distal end and defining a first axis, said proximal end having a neck region which joins the stem at a juncture, said stem having anterior, posterior, medial and lateral surfaces and said surfaces tapering from said proximal end toward said distal end, a groove in the vicinity of said proximal end in each of said anterior, medial and posterior surfaces; and (b) a spacer positioned in said groove and extending outwardly from each of said anterior, medial and posterior surfaces, said spacer including a skirt extending from a proximal end in the vicinity of said groove to a distal end, said skirt having an anterior wall portion, a medial wall portion and a posterior wall portion in contact, respectively, with each of said stem anterior, medial and posterior surfaces, said skirt being provided with an outwardly extending flange at said distal end.

10. A femoral hip joint prosthesis according to claim 9 wherein said skirt is provided with at least one slot extending from said distal end toward said proximal end.

11. In combination (a) a femoral hip joint prosthesis having an elongated stem extending from a proximal end to a distal end, said stem having anterior, posterior, medial and lateral surfaces convergently tapering from said proximal end toward said distal end, a distally facing shoulder in the vicinity of said proximal end in each of said anterior and posterior surfaces; and (b) a spacer engaged to said stem in abutting relationship with said shoulder, said spacer extending outwardly from each of said anterior, medial and posterior surfaces and including a skirt extending from a proximal end abutting said shoulder to a distal end, said skirt having an anterior wall portion, a medial wall portion and a posterior wall portion in contact, respectively, with each of said stem anterior, medial and posterior surfaces and having a flange at said skirt proximal end extending outwardly from each of said anterior wall portion, medial wall portion and posterior wall portion.

12. The combination according to claim 11 wherein said skirt is provided with apertures.

13. In combination
(a) a femoral hip joint prosthesis having an elongated stem extending from a proximal end to a distal end, said stem having anterior, posterior, medial and lateral surfaces convergently tapering from said proximal end toward said distal end, a distally facing shoulder in the vicinity of said proximal end in each of said anterior and posterior surfaces; and
(b) a spacer engaged to said stem in abutting relationship with said shoulder, said spacer extending outwardly from each of said anterior, medial and posterior surfaces and including a skirt extending from a proximal end abutting said shoulder to a distal end, said skirt having an anterior wall portion, a medial wall portion and a posterior wall portion in contact, respectively, with each of said stem anterior, medial and posterior surfaces and having apertures comprising slots extending from said skirt distal end toward said skirt proximal end.

14. In combination
(a) a femoral hip joint prosthesis having an elongated stem extending from a proximal end to a distal end, said stem having anterior, posterior, medial and lateral surfaces convergently tapering from said proximal end toward said distal end, a distally facing shoulder in the vicinity of said proximal end in each of said anterior and posterior surfaces; and
(b) a spacer engaged to said stem in abutting relationship with said shoulder, said spacer extending outwardly from each of said anterior, medial and posterior surfaces and including a skirt extending from a proximal end abutting said shoulder to a distal end, said skirt having an anterior wall portion, a medial wall portion and a posterior wall portion in contact, respectively, with each of said stem anterior, medial and posterior surfaces and having apertures comprising elongated slots spaced from said skirt distal end.

15. In combination
(a) a femoral hip joint prosthesis having an elongated stem extending from a proximal end to a distal end, said stem having anterior, posterior, medial and lateral surfaces convergently tapering from said proximal end toward said distal end, a distally facing shoulder in the vicinity of said proximal end in each of said anterior and posterior surfaces; and
(b) a spacer engaged to said stem in abutting relationship with said shoulder, said spacer extending outwardly from each of said anterior, medial and posterior surfaces and including a skirt extending from a proximal end abutting said shoulder to a distal end, said skirt having an anterior wall portion, a medial wall portion and a posterior wall portion in contact, respectively, with each of said stem anterior, medial and posterior surfaces and having apertures, said skirt being provided with an outwardly extending flange at said distal end.

16. The combination according to claim 15 wherein said skirt is provided with an outwardly extending flange at said distal end.

17. The combination according to claim 11 wherein said skirt is provided with an outwardly extending flange at said distal end.

18. The combination according to claim 17 wherein said skirt is provided with at least one slot extending from said distal end toward said proximal end.

19. In combination
(a) a femoral hip joint prosthesis having an elongated stem extending from a proximal end to a distal end, said stem having anterior, posterior, medial and lateral surfaces convergently tapering from said proximal end toward said distal end, a distally facing shoulder in the vicinity of said proximal end in each of said anterior and posterior surfaces;
(b) a spacer engaged to said stem in abutting relationship with said shoulder, said spacer extending outwardly from each of said anterior, medial and posterior surfaces; and
(c) a second spacer engaged to said stem distal end, said second spacer having a wall portion extending toward said stem proximal end in contact with said stem to a free end, said wall portion having at least one slot extending from said free end.

20. The combination according to claim 19 wherein said free end has an outwardly extending flange.

21. In combination
(a) a femoral hip joint prosthesis having an elongated stem extending from a proximal end to a distal end, said stem having anterior, posterior, medial and lateral surfaces convergently tapering from said proximal end toward said distal end, a distally facing shoulder in the vicinity of said proximal end in each of said anterior and posterior surfaces;
(b) a first spacer engaged to said stem in abutting relationship with said shoulder, said first spacer extending outwardly from each of said anterior, medial and posterior surfaces; and
(c) a second spacer engaged to said stem distal end, said second spacer having a wall portion extending toward said stem proximal end in contact with said stem to a free end.

22. A spacer for use in maintaining a space to receive bone cement adjacent the anterior, medial and posterior surfaces of a femoral hip joint prosthesis comprising a skirt extending from a proximal end to a distal end, said skirt having an anterior wall portion, a medial wall portion and a posterior wall portion intended for contact, respectively, with each of said stem anterior, medial and posterior surfaces, each of said anterior, medial and posterior wall portions having a flange at said proximal end.

23. A spacer according to claim 22 wherein said skirt includes a first portion extending from said anterior wall portion toward said posterior wall portion and a second portion extending from said posterior wall portion toward said anterior wall portion said first portion and said second portion being in spaced relationship.

24. A spacer according to claim 22 wherein said flange at said skirt proximal end extends outwardly from each of said anterior wall portion, medial wall portion and posterior wall portion.

25. A spacer according to claim 22 wherein said flange extends inwardly from each of said anterior wall portion, medial wall portion and posterior wall portion.

26. A spacer according to claim 22 wherein said skirt is provided with apertures.

27. A spacer according to claim 26 wherein said apertures comprise slots extending from said skirt distal end toward said skirt proximal end.

28. A spacer according to claim 26 wherein said apertures comprise elongated slots spaced from said skirt distal end.

29. A spacer according to claim 22 wherein said apertures extend from said skirt proximal end toward said skirt distal end.

30. A spacer according to claim 22 wherein said flange extends both inwardly and outwardly from each of said anterior wall portion, medial wall portion and posterior wall portion.

31. A spacer for use in maintaining a space to receive bone cement adjacent the anterior, medial and posterior surfaces of a femoral hip joint prosthesis comprising a skirt extending from a proximal end to a distal end, said skirt having an anterior wall portion, a medial wall portion and a posterior wall portion intended for contact, respectively, with each of said stem anterior, medial and posterior surfaces, said spacer having a first flange extending outwardly from skirt at said proximal end and a second flange extending outwardly from said skirt at said distal end.

32. A femoral hip joint prosthesis for use in combination with bone cement comprising an elongated stem extending from a proximal end to a distal end and defining a first axis, said proximal end having a neck region which joins the stem at a juncture, said stem having anterior, posterior, medial and lateral surfaces and said surfaces tapering from said proximal end toward said distal end, a groove in the vicinity of said proximal end in each of said anterior, medial and posterior surfaces, each said groove in said anterior surface and said posterior surface extending substantially throughout the entire distance from said lateral surface to said medial surface, a spacer positioned in and substantially filling said groove and extending outwardly from each of said anterior, posterior and medial surfaces a distance of 0.5 to 3 millimeters, but no greater than the maximum thickness of bone cement in any area.

33. In combination (a) a femoral hip joint prosthesis, (b) a spacer and (c) bone cement, said prosthesis comprising an elongated stem extending from a proximal end to a distal end and defining a first axis, said proximal end having a neck region which joins the stem at a juncture, said stem having anterior, posterior, medial and lateral surfaces and said surfaces tapering from said proximal end toward said distal end, a groove in the vicinity of said proximal end in each of said anterior, medial and posterior surfaces, each said groove in said anterior surface and said posterior surface extending substantially throughout the entire distance from said lateral surface to said medial surface, said bone cement encapsulating said stem from said distal end to an area substantially aligned with said groove, said spacer positioned in and substantially filling said groove and extending outwardly from each of said anterior, medial and posterior surfaces a distance at least equal to the intended thickness of said bone cement but no greater than the maximum thickness of bone cement in any area.

34. A femoral hip joint prosthesis according to claim 33 wherein said spacer extends outwardly from each of said anterior, posterior and medial surfaces a distance of 0.5 to 3 millimeters.

* * * * *